US011600380B2

(12) United States Patent
 Martindale et al.

(10) Patent No.: US 11,600,380 B2
(45) Date of Patent: Mar. 7, 2023

(54) DECISION SUPPORT TOOL FOR DETERMINING PATIENT LENGTH OF STAY WITHIN AN EMERGENCY DEPARTMENT

(71) Applicant: CERNER INNOVATION, INC., Kansas City, KS (US)

(72) Inventors: J. D. Martindale, Kansas City, KS (US); Andrew Roberts, Overland Park, KS (US); Sasanka Are, Kansas City, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 330 days.

(21) Appl. No.: 16/728,306

(22) Filed: Dec. 27, 2019

(65) Prior Publication Data

US 2020/0211701 A1    Jul. 2, 2020

Related U.S. Application Data

(60) Provisional application No. 62/786,719, filed on Dec. 31, 2018.

(51) Int. Cl.
 *G16H 40/20*    (2018.01)
 *G06Q 10/0631*    (2023.01)
 (Continued)

(52) U.S. Cl.
 CPC .............. *G16H 40/20* (2018.01); *G06N 20/00* (2019.01); *G06Q 10/063116* (2013.01); *G06Q 10/063118* (2013.01); *G16H 10/60* (2018.01)

(58) Field of Classification Search
 CPC ........ G16H 40/20; G16H 50/70; G16H 15/00; G16H 50/20
 See application file for complete search history.

(56) References Cited

U.S. PATENT DOCUMENTS

2019/0180868 A1*  6/2019  Makram ................ G16H 10/60
2020/0013490 A1*  1/2020  Rumoro ................ G16H 40/63
2020/0082941 A1*  3/2020  Wang ..................... G16H 50/20

FOREIGN PATENT DOCUMENTS

WO    WO-2018112185 A1 *  6/2018  ............. G06Q 50/22

OTHER PUBLICATIONS

Patients Discharged from the Emergency Department-Using an Accelerated Failure Time Model, Chaou CH, Chen HH, Chang SH, Tang P, Pan SL, et al. (2017) Predicting Length of Stay among Patients Discharged from the Emergency Department—Using an Accelerated Failure Time Model. PLOS ONE 12(1): e0165756. (Year: 2017).*

(Continued)

*Primary Examiner* — Joseph D Burgess
(74) *Attorney, Agent, or Firm* — Invoke

(57) ABSTRACT

A decision support tool is provided for predicting a patient's length of stay within a healthcare unit, such as the emergency department. The predicted length of stay may be determined using patient information and facility information, which includes information about the department and the facility in which the department is located. The patient information and the facility information may be used to determine feature values input into a plurality of machine learning models. The models may be used sequentially such that initial models are used to predict variables relating to the patient's length of stay and output of such models is used with a length-of-stay model to determine the predicted length of stay. One or more response actions may be automatically initiated based on the predicted length of stay. Such response actions may include resource management actions to allocate resources within the healthcare unit.

19 Claims, 12 Drawing Sheets

(51) Int. Cl.
  *G16H 10/60* (2018.01)
  *G06N 20/00* (2019.01)

(56) References Cited

OTHER PUBLICATIONS

Predicting hospital length-of-stay attime of admission, Cummings D, Towards Data Science, Dec. 15, 2018 (Year: 2018).*
B. Graham, R. Bond, M. Quinn and M. Mulvenna, "Using Data Mining to Predict Hospital Admissions From the Emergency Department," in IEEE Access, vol. 6, pp. 10458-10469, 2018 (Year: 2018).*

* cited by examiner

DECISION SUPPORT TOOL FOR DETERMINING PATIENT LENGTH OF STAY WITHIN AN EMERGENCY DEPARTMENT

CROSS-REFERENCE TO RELATED APPLICATIONS

This application, Ser. No. 16/728,306 and entitled "Decision Support Tool for Determining Patient Length of Stay Within an Emergency Department," claims priority to U.S. Provisional Patent Application No. 62/786,719, filed Dec. 31, 2018, entitled, "Decision Support Tool for Determining Patient Length of Stay Within an Emergency Department," the entirety of which is incorporated here by reference.

BACKGROUND

For certain departments within a healthcare facility, such as the emergency department, the volume of patients changes frequently, and the volume at any current time will depend on the length of time each person stays in the department. Longer lengths of stays can result in congestion, poor patient outcomes, inefficient resource utilization, and staff stress and burnout. Predicting the length of time of each person's stay can help estimate the volume of the department at a future time and, consequently, can be used for more efficient and effective allocation of resources, such as staffing, beds, equipment, medications, and the like. In turn, more efficient allocation of resources can help to reduce lengths of stays, which can ultimately lead to better patient outcomes. For a department like the emergency department where there is a wide variety of patients and healthcare concerns, the length of a stay is very context specific and is based on several factors relating to the patient and the state of the department and healthcare facility. Conventional technologies for determining a length of stay consider only one factor at a time, which results in less accurate and less useful predictions.

SUMMARY

This summary is provided to introduce a selection of concepts in a simplified form that are further described below in the detailed description. This summary is not intended to identify key features or essential features of the claimed subject matter, nor is it intended to be used in isolation as an aid in determining the scope of the claimed subject matter.

Improved monitoring and decision support technology is provided for predicting lengths of stays for patients within a discrete healthcare department, such as the emergency department, and, in some embodiments, utilizing the predictions to automatically and appropriately allocate (or generate a recommended allocation of) department resources in accordance with the expected volume of patients within a future time interval. In particular, a decision support system is provided for predicting a likely length of stay for a particular patient admitted or seeking admittance into the department. Predicted lengths of stay for multiple patients may be used to estimate patient volume within the department at a future time, which can then be used to allocate the appropriate resources, including staff, beds, medications, equipment, and supplies, for that future time. A decision support tool for managing resources in accordance with this disclosure may also include a graphical user interface having user interface elements visually representing one or more resource measurements based on the predicted of lengths of stays.

As described herein, the lengths of stays may be predicted using a plurality of machine learning models. In exemplary embodiments, sequential modeling is performed in which predictions for variables relating to a patient's stay are made using a plurality of machine learning models, and the outputs from those models are used to predict a length of stay with a length-of-stay model. A plurality of features used as input for the models are determined from patient information and facility information such that multiple factors affecting length of stay are taken into consideration for the patient. In this way, the length of stay may be more accurately predicted through embodiments of the disclosure than through conventional methods. Accordingly, one aim of the embodiments of this disclosure is to improve upon conventional industry practice by deriving accurate predictive capabilities for lengths of stays to provide more efficient management of resources, which, in turn, may positively improve the quality of care given to patients.

BRIEF DESCRIPTION OF THE DRAWINGS

The present invention is described in detail below with reference to the attached drawing figures, wherein.

DETAILED DESCRIPTION

Figure 1A:
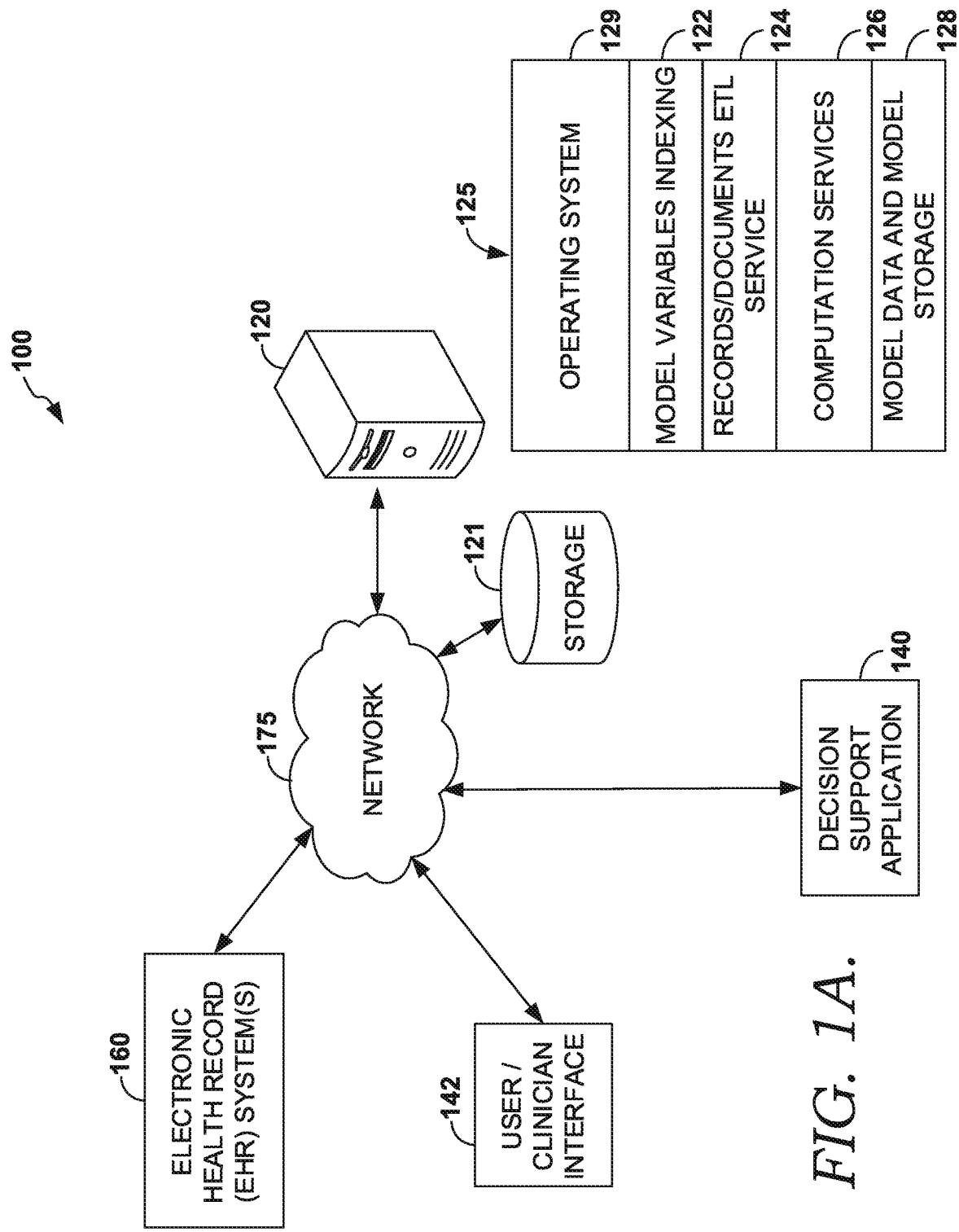
FIGS. 1A and 1B depict aspects of an illustrative operating environment suitable for practicing an embodiment of the disclosure.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media, as discussed further with respect to FIGS. 1A-1B.

Accordingly, at a high level, this disclosure describes, among other things, methods and systems for predicting a patient's length of stay in a healthcare unit, such as the emergency department. In exemplary embodiments, a length of stay is the time interval between registration or admittance into a healthcare unit, such as the emergency department, and leaving the unit. The patient's length of stay may be predicted using a sequential modeling technique by applying multiple machine learning models to make predictions for a plurality of patient variables relating to the patient's stay. The predicted variable, also referred to as features, may be based on patient information and facility information and used to predict the length of stay. In some embodiments, the methods and systems may be implemented as a decision support computer application or tool for providing support for allocation of resources within the department. For instance, predictions for multiple patients may be combined to estimate a likely volume of patients within the department at a future time and identify resources, such as staff, space, medicine, supplies, and equipment, that will be needed for that future time.

As previously explained, the volume of patients within certain healthcare units, such as the emergency department, can vary widely over time, and this variance makes it difficult to effectively manage physical resources, such as staff, space, supplies, medicine, and equipment. Inefficient resources can cause longer patient stays, which, in turn, can result in congestion, poor patient outcomes, further inefficient resource utilization, and staff stress and burnout.

Because the lengths of patient stays ultimately affects patient volume, predicting the lengths of stays can be used to predict patient volume within the department and, thus, to better manage resources for a future time interval. Current proposals for predicting lengths of stays take into consideration only a single factor at a time; however, for many care units like the emergency department, a length of stay is very context specific based on several factors relating to both the patient and the status of the department and/or facility. Therefore, the current proposals for predicting lengths of stay do not provide an account prediction for use in effective resource management.

Accordingly, one aim of embodiments of this disclosure is to improve upon conventional industry technology by deriving more accurate predictive capabilities for length of stay for more effective management of resources and, ultimately, improved patient care. Specifically, embodiments include receiving patient information for a patient being registered or admitted into an emergency department and facility information for a facility in which the emergency department is located. Sequential modeling may be performed on the patient information and the facility information to predict the patient's length of stay in the emergency department. Sequential modeling includes using a plurality of machine learning models and using outputs of at least some of the models to make predictions with another model. Outputs of initial models may include a probability of the patient being admitted into an inpatient unit of the facility, a probability the patient will need a telemetry bed, and a probability that the inpatient unit in which the patient is admitted is a specialized unit. Based on the length of stay predicted for the patient, one or more response actions may be initiated. A response action may include transmitting an electronic notification of the patient's predicted length of stay to a remote user device. The response actions may also include a resource management action, which may include requesting additional staff, medications, supplies, equipment, or space, or allocating such resources to other units if they will not be needed.

Further embodiments include making predictions for lengths of stays for a plurality of patients who have been registered within the emergency department. The lengths of stays predicted for the plurality of patients may be used to estimate a patient volume within the emergency department for a future time interval. Further, one or more response actions, including resource management actions, may be automatically initiated based on the estimated patient volume for the future time interval.

In yet a further embodiment, a graphical user interface may be generated for rendering on a display component of a user device with the user interface including user interface elements visually representing one or more resource measurements for a future time interval based on predicted lengths of stays. For instance, the graphical user interface may include one or more elements representing available resources, such as patient beds and staff, for a particular time interval. The user interface elements may further include selectable or otherwise actionable items to facilitate the reallocation of resources, such as for making requests for additional resources.

Referring now to the drawings generally and, more specifically, referring to FIG. 1A, an aspect of an operating environment 100 is provided suitable for practicing an embodiment of this disclosure. Certain items in block-diagram form are shown more for being able to reference something consistent with the nature of a patent rather than to imply that a certain component is or is not part of a certain device. Similarly, although some items are depicted in the singular form, plural items are contemplated as well (e.g., what is shown as one data store might really be multiple data stores distributed across multiple locations). But showing every variation of each item might obscure aspects of the invention. Thus, for readability, items are shown and referenced in the singular (while fully contemplating, where applicable, the plural).

As shown in FIG. 1A, example operating environment 100 provides an aspect of a computerized system for compiling and/or running an embodiment of a computer-decision support tool for predicting a length of a patient stay. Operating environment 100 includes one or more electronic health record (EHR) systems, such as hospital EHR system 160, communicatively coupled to network 175, which is communicatively coupled to computer system 120. In some embodiments, components of operating environment 100 that are shown as distinct components may be embodied as part of or within other components of operating environment 100. For example, EHR systems 160 may comprise one or more EHR systems, such as hospital EHR systems, health information exchange EHR systems, ambulatory clinic EHR systems, and psychiatry/neurology EHR systems. Such EHR systems may be implemented in computer system 120. Similarly, EHR system 160 may perform functions for two or more of the EHR systems (not shown).

Network 175 may comprise the Internet, and/or one or more public networks, private networks, other communications networks such as a cellular network, or a similar network for facilitating communication among devices connected through the network. In some embodiments, network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown as being communicatively coupled to network 175 may be directly communicatively coupled to other items shown communicatively coupled to network 175.

In some embodiments, operating environment 100 may include a firewall (not shown) between a first component and network 175. In such embodiments, the firewall may reside on a second component located between the first component and network 175, such as on a server (not shown), or reside on another component within network 175, or may reside on or as part of the first component.

Embodiments of EHR system 160 include one or more data stores of health records, which may be stored on storage 121, and may further include one or more computers or servers that facilitate the storing and retrieval of health records. In some embodiments, EHR system 160 may be implemented as a cloud-based platform or may be distributed across multiple physical locations. EHR system 160 may further include record systems that store real-time or near real-time patient (or user) information, such as wearable, bedside, or in-home patient monitors, for example. Although FIG. 1A depicts an exemplary EHR system 160 that may be used for storing patient information, it is contemplated that an embodiment may also rely on decision support application 140 and/or monitor 141 for storing and retrieving patient record information, such as information acquired from monitor 141.

Example operating environment 100 further includes a provider user/clinician interface 142 communicatively coupled through network 175 to EHR system 160. Although operating environment 100 depicts an indirect communicative coupling between user/clinician interface 142 and EHR system 160 through network 175, it is contemplated that an embodiment of user/clinician interface 142 is communicatively coupled to EHR system 160 directly. An embodiment of user/clinician interface 142 takes the form of a graphical user interface operated by a software application or set of applications (e.g., decision support application 140) on a computing device. In an embodiment, the application includes the PowerChart® software manufactured by Cerner Corporation. In an embodiment, the application is a Web-based application or applet. A healthcare provider application may facilitate accessing and receiving information from a user or healthcare provider about a specific patient or set of patients for which the lengths of stays within a healthcare unit, such as the emergency department, are determined according to the embodiments presented herein. Embodiments of user/clinician interface 142 also facilitate accessing and receiving information from a user or healthcare provider about a specific patient or population of patients including patient history; healthcare resource data; physiological variables (e.g., vital signs), measurements, time series, and predictions (including plotting or displaying the determined outcome and/or issuing an alert) described herein; or other health-related information, and facilitates the display of results, recommendations, or orders, for example. In an embodiment, user/clinician interface 142 also facilitates receiving orders, such as orders for more resources, from a user based on the results of predictions. User/clinician interface 142 may also be used for providing diagnostic services or evaluation of the performance of various embodiments.

An embodiment of decision support application 140 comprises a software application or set of applications (which may include programs, routines, functions, or computer-performed services) residing on a client computing device, on one or more servers in the cloud, or distributed in the cloud and on a client computing device such as a personal computer, laptop, smartphone, tablet, mobile computing device, front-end terminals in communication with back-end computing systems, or other computing device(s) such as computer system 120 described below. In an embodiment, decision support application 140 includes a Web-based application or applet (or set of applications) usable to provide or manage user services provided by an embodiment of the invention. For example, in an embodiment, decision support application 140 facilitates processing, interpreting, accessing, storing, retrieving, and communicating information acquired from monitor 141, EHR system 160, or storage 121, including predictions and condition evaluations determined by embodiments of the invention as described herein. In an embodiment, decision support application 140 sends a recommendation or notification (such as an alarm or other indication) directly to user/clinician interface 142 through network 175. In an embodiment, application 140 sends a maintenance indication to user/clinician interface 142. In some embodiments, application 140 includes or is incorporated into a computerized decision support tool, as described herein. Further, some embodiments of application 140 utilize user/clinician interface 142. For instance, in one embodiment of application 140, an interface component, such as user/clinician interface 142, may be used to facilitate access by a user (including a clinician/caregiver or patient) to functions or information on monitor 141, such as operational settings or parameters, user identification, user data stored on monitor 141, and diagnostic services or firmware updates for monitor 141, for example.

In some embodiments, application 140 and/or interface 142 facilitates accessing and receiving information from a user or healthcare provider about a specific patient, a set of patients, or a population according to the embodiments presented herein. Such information may include historical data; healthcare resource data; variables, measurements, time series, and predictions (including plotting or displaying the determined outcome and/or issuing an alert) described herein; or other health-related information. Application 140 and/or interface 142 also facilitates the display of results, recommendations, or orders, for example. User interface 142 may also facilitate receiving information from a user or care provider, including a department manager, about the state of a facility and/or department. In an embodiment, application 140 also facilitates receiving orders, staffing scheduling, or queries from a user, based on the results of the forecasted outputs, which may utilize user interface 142 in some embodiments.

Decision support application 140 may also be used for providing diagnostic services or evaluation of the performance of various embodiments. As shown in example operating environment 100, in one embodiment, decision support application 140, or the computer system on which it operates, is communicatively coupled to monitor 141 via network 175. In an embodiment, patient monitor 141 communicates directly (or via network 175) to computer system 120 and/or user/clinician interface 142. In an embodiment, monitor 141 (sometimes referred to herein as a patient-interface component) comprises one or more sensor components operable to acquire clinical or physiological information about a patient, such as various types of physiological measurements, physiological variables, or similar clinical information associated with a particular physical or mental state of the patient. Such clinical or physiological information may be acquired by monitor 141 periodically, continuously, as needed, or as they become available, and may be represented as one or more time series of measured variables. It is also contemplated that the clinical or physiological information about a patient or population of patients, such as the monitored variables, patient demographics, patient history, and/or clinical narratives regarding the patient, used according to the embodiment of the invention disclosed herein may be received from a patient's historical data in EHR system 160, or from human measurements, human observations, or automatically determined by sensors in proximity to the patient.

An embodiment of monitor 141 stores user-derived data locally or communicates data over network 175 to be stored remotely. In an embodiment, decision support application 140, or the computer system it is operating on, is wirelessly communicatively coupled to monitor 141. Application 140 may also be embodied as a software application or app operating on a user's mobile device, as described above. In an embodiment, application 140 and monitor 141 are functional components of the same device, such as a device comprising a sensor, an application, and a user interface. In an embodiment, decision support application 140 is in communication with or resides on a computing system that is embodied as a base station, which may also include functionality for charging monitor 141 or downloading information from monitor 141.

Example operating environment 100 further includes computer system 120, which may take the form of a server, which is communicatively coupled through network 175 to EHR system 160, and storage 121. Computer system 120 comprises one or more processors operable to receive instructions and process them accordingly and may be embodied as a single computing device or multiple computing devices communicatively coupled to each other. In one embodiment, processing actions performed by computer system 120 are distributed among multiple locations such as one or more local client devices and one or more remote servers and may be distributed across the other components of example operating environment 100. For example, a portion of computer system 120 may be embodied on monitor 141 or the computer system supporting application 140 for performing signal conditioning of a measured patient variable. In one embodiment, computer system 120 comprises one or more computing devices, such as a server, desktop computer, laptop, or tablet, cloud-computing device or distributed computing architecture, a portable computing device such as a laptop, tablet, ultra-mobile PC, or a mobile phone.

Embodiments of computer system 120 include computer software stack 125, which, in some embodiments, operates in the cloud as a distributed system on a virtualization layer within computer system 120, and includes operating system 129. Operating system 129 may be implemented as a platform in the cloud and is capable of hosting a number of services such as services 122, 124, 126, and 128, described further herein. Some embodiments of operating system 129 comprise a distributed adaptive agent operating system. Embodiments of services 122, 124, 126, and 128 run as a local or distributed stack in the cloud, on one or more personal computers or servers such as computer system 120, and/or a computing device running interface 142 and/or decision support application 140. In some embodiments, user/clinician interface 142 and/or decision support application 140 operate in conjunction with software stack 125.

In embodiments, model variables indexing service 122 provides services that facilitate retrieving frequent itemsets, extracting database records, and cleaning the values of variables in records. For example, service 122 may perform functions for synonymic discovery, indexing or mapping variables in records, or mapping disparate health systems' ontologies, such as determining that a particular medication frequency of a first record system is the same as another record system. In some embodiments, model variables indexing service 122 may invoke computation services 126. Predictive models service 124 is generally responsible for providing one or more models for predicting length of stay as described in connection to methods 200 and 500 of FIGS. 2 and 5, respectively.

Computation services 126 perform statistical software operations, such as computing the transformed variable predictions and engineered features as described herein. In an embodiment, computation services 126 and predictive models service 124 include computer software services or computer program routines. Computation services 126 also may include natural language processing services (not shown), such as Discern nCode™ developed by Cerner Corporation, or similar services. In an embodiment, computation services 126 include the services or routines that may be embodied as one or more software agents or computer software routines. Computation services 126 also may include services or routines for utilizing performing sequential modeling using one or more models, including decision trees and logistic models, for predicting lengths of patient stays, such as the models described in connection to FIGS. 2-8.

In some embodiments, stack 125 includes file system or cloud-services 128. Some embodiments of file system/cloud-services 128 may comprise an Apache Hadoop and Hbase framework or similar frameworks operable for providing a distributed file system and which, in some embodiments, provide access to cloud-based services such as those provided by Cerner HealtheIntent®. Additionally, some embodiments of file system/cloud-services 128 or stack 125 may comprise one or more stream processing services (not shown). For example, such stream processing services may be embodied using IBM InfoSphere stream processing platform, Twitter Storm stream processing, Ptolemy or Kepler stream processing software, or similar complex event processing (CEP) platforms, frameworks, or services, which may include the use of multiple such stream processing services (in parallel, serially, or operating independently). Some embodiments of the invention also may be used in conjunction with Cerner Millennium®, Cerner CareAware® (including CareAware iBus®), Cerner CareCompass®, or similar products and services.

Example operating environment 100 also includes storage 121 (or data store 121), which, in some embodiments, includes patient data for a candidate or target patient (or information for multiple patients), including raw and processed patient data; variables associated with patient recommendations; recommendation knowledge base; recommendation rules; recommendations; recommendation update statistics; an operational data store, which stores events, frequent itemsets (such as, for example, "X often happens with Y"), and itemsets index information; association rulebases; agent libraries, solvers and solver libraries, and other similar information including data and computer-usable instructions; patient-derived data; and healthcare provider information, for example. It is contemplated that the term "data" used herein includes any information that can be stored in a computer-storage device or system, such as user-derived data, computer usable instructions, software applications, or other information. In some embodiments, storage 121 comprises data store(s) associated with EHR system 160. Further, although depicted as a single storage store, storage 121 may comprise one or more data stores, or may be in the cloud.

Figure 1B:
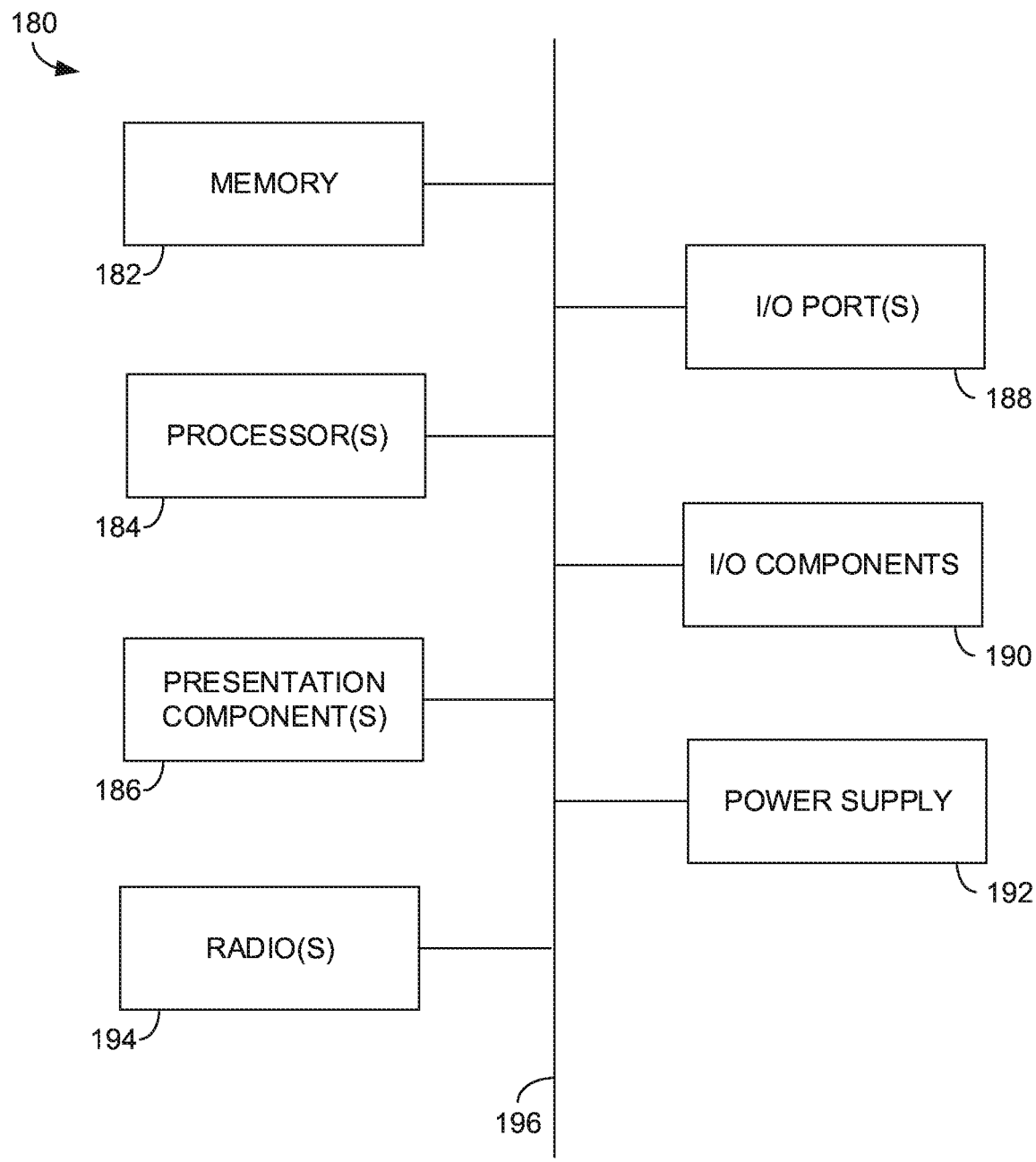

Turning briefly to FIG. 1B, there is shown one example embodiment of computing system 180 representative of a system architecture that is suitable for computer systems such as computer system 120. Computing system 180 includes a bus 196 that directly or indirectly couples the following devices: memory 182, one or more processors 184, one or more presentation components 186, input/output (I/O) ports 188, input/output components 190, radio 194, and an illustrative power supply 192. Bus 196 represents what may be one or more busses (such as an address bus, data bus, or combination thereof). Although the various blocks of FIG. 1A are shown with lines for the sake of clarity, in reality, delineating various components is not so clear, and metaphorically, the lines would more accurately be grey and fuzzy. For example, one may consider a presentation component, such as a display device, to be an I/O component. Also, processors have memory. As such, the diagram of FIG. 1A is merely illustrative of an exemplary computing system that can be used in connection with one or more embodiments of the present invention. Distinction is not made between such categories as "workstation," "server," "laptop," "hand-held device," etc., as all are contemplated within the scope of FIG. 1A and reference to "computing system."

Computing system 180 typically includes a variety of computer-readable media. Computer-readable media can be any available media that can be accessed by computing system 180 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing system 180. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above should also be included within the scope of computer-readable media.

Memory 182 includes computer-storage media in the form of volatile and/or nonvolatile memory. The memory may be removable, non-removable, or a combination thereof. Exemplary hardware devices include solid-state memory, hard drives, optical-disc drives, etc. Computing system 180 includes one or more processors that read data from various entities such as memory 182 or I/O components 192. Presentation component(s) 188 present data indications to a user or other device. Exemplary presentation components include a display device, speaker, printing component, vibrating component, etc.

In some embodiments, computing system 180 comprises radio(s) 196 that facilitates communication with a wireless-telecommunications network. Illustrative wireless telecommunications technologies include CDMA, GPRS, TDMA, GSM, and the like. Radio 196 may additionally or alternatively facilitate other types of wireless communications including Wi-Fi, WiMAX, LTE, or other VoIP communications. As can be appreciated, in various embodiments, radio 196 can be configured to support multiple technologies and/or multiple radios can be utilized to support multiple technologies.

I/O ports 190 allow computing system 180 to be logically coupled to other devices, including I/O components 192, some of which may be built in. Illustrative components include a microphone, joystick, game pad, satellite dish, scanner, printer, wireless device, etc. The I/O components 192 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing system 180. The computing system 180 may be equipped with depth cameras, such as stereoscopic camera systems, infrared camera systems, RGB camera systems, touchscreen technology, and combinations of these, for gesture detection and recognition. Additionally, the computing system 180 may be equipped with accelerometers or gyroscopes that enable detection of motion.

The architecture depicted in FIG. 1B is provided as one example of any number of suitable computer architectures, such as computing architectures that support local, distributed, or cloud-based software platforms, and are suitable for supporting computer system 120.

Returning to FIG. 1A, in some embodiments, computer system 120 is a computing system made up of one or more computing devices. In some embodiments, computer system 120 includes one or more software agents and, in an embodiment, includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

Figure 2:
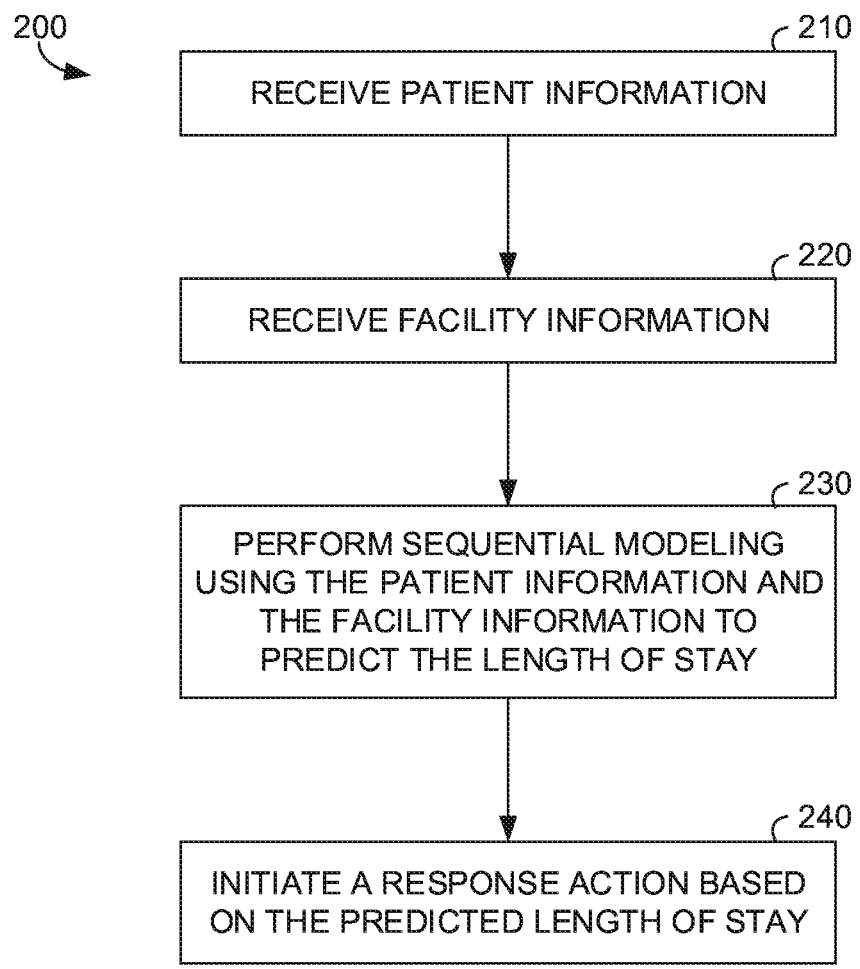
FIG. 2 depicts a flow diagram of a method for predicting a patient's length of stay within the emergency department and suitable for implementation in a decision support system, in accordance with an embodiment of the disclosure.

Turning now to FIG. 2, an example embodiment of a method for predicting a patient's length of stay is provided and is referred to generally as method 200. In particular, example method 200 utilizes patient information and facility information with a plurality of machine learning models to predict an amount of time a patient is expected to remain within a specific healthcare department or unit. In some embodiments, method 200 is suitable for implementation as a computer-performed decision support tool or application for managing clinician and facility resources based on more predicted lengths of stays that are more accurate than conventional technology would otherwise allow.

In accordance with method 200, at step 210, a plurality of patient information is received. The patient information may comprise current patient data, patient demographic data, and/or historical patient data. In exemplary aspects, current patient data includes data relating to the patient's current condition as well as the patient's current visit to the healthcare unit, such as the emergency department. The patient's current condition may include any current clinical conditions that the patient has, whether the patient is pregnant, and values for one or more physiological variables, such as heart rate, blood pressure, weight, height, body mass index, temperature, and the like. Current patient data about the present visit may include the patient's arrival time, and the mode of arrival (e.g., whether the patient arrived via ambulance).

Patient demographics may include age, sex, race, nationality, socioeconomic status, marital status, and/or employment status. This data may further include the patient's insurance information, such as the insurance provider and the type of plan. Further, historical patient data may include the patient's medical history and/or family history. Historical patient data may also include information about the patient's past visits to the particular facility department, such as a number of times or frequency that the patient has visited the emergency department; whether or how often the patient has previously left before being discharged or seen by a clinician; whether or how often the patient is admitted into another unit, such as an inpatient unit; and past lengths of stays.

This patient information may be received from different sources. For instance, in one embodiment, all patient data is received at step 210 from the patient's EMR. In other embodiments, data relating to the patient's current condition and/or patient demographics may be received directly from a user, such as the patient or a care provider, inputting such information into a user device when the patient is at registration or triage in an emergency department. Some current patient data, such as patient variable values, may be received from one or more sensors or monitoring devices. Additionally, historical patient information may be received from the patient's EMR and/or from insurance claims data for the patient. In an alternative embodiment, the patient's history may be received directly from the patient during registration.

Further, at step 220, a plurality of facility information may be received. As used herein, facility information refers to both information relating to the particular department the patient is visiting (such as an emergency department) and information relating to the facility in which the department is located. As such, facility information may include the current patient volume in the department; current patient volume in other departments within the facility, such as inpatient units; current staffing levels, staffing levels scheduled for a future time interval; current supply, equipment, and/or medication levels; and expected supply equipment, and/or medication levels for a future time interval.

Facility information may also include a patient's current queue position, indicating the order in which the patient will be seen relative to other people. Although the queue position may be for a particular patient, this information may be based on the acuity of other patients waiting to be seen or treated. As such, the queue position may be determined by the number of patients within the department having an acuity level greater than or equal to the acuity level of the particular patient. Acuity levels may be assigned to patients during triage or registration. Facility information may be received from one or more databases, such as storage 121 in FIG. 1A, or may be received directly through user input or from monitors/sensors.

At step 230, the patient's length of stay in the department is predicted using a plurality of machine learning models on least some of the patient information and the facility information. In exemplary aspects, the prediction is generated using sequential modeling. As used herein, sequential modeling refers to applying a plurality of models in a sequence such that the output of at least one model is used as input, either as the original output or transformed output, in another model. For example, in an example embodiment, a first model is used to calculate the probability that the patient will be admitted into an inpatient unit (rather than being discharged), and that probability, along with other data, may be used as input into a model for predicting the patient's length of stay in the current department, such as the emergency department.

In exemplary aspects, the patient information and/or the facility information is used to predict a plurality of features with a plurality of initial models, and the predicted features may then be used to predict the patient's length of stay using the length-of-stay model. For instance, in an example embodiment, at least some of the patient information and facility information is used with a first model to determine probability that the patient will be admitted as an inpatient (rather than being discharged), with a second model to determine a probability that the patient will be admitted into an unspecialized unit within the facility, and with a third model to determine a probability that the patient will need a telemetry bed. Outputs (i.e., the predictions) from the initial models may be input directly into the model predicting length of stay or may be transformed before being input into the length-of-stay model. In exemplary embodiments, for instance, the log odds of the initial predictions are determined and used as transformed features for the length-of-stay model.

In some embodiments, the initial models work sequentially with one another as well as the length-of-stay model. In this way, an initial prediction from one model may be used to predict another feature using another model before both such initial predictions are used to predict a patient's length of stay. For instance, in some embodiments, patient and facility information is used with an admission model to predict whether a particular patient will be admitted into an inpatient department, will walk out of the emergency department, and/or will be transferred to another facility. One or more probabilities from the admission model may be used, along with certain patient and facility information, to predict a likelihood of admission into certain facility units, such as a specialized unit and/or one with telemetry beds. The probabilities from the admission model and facility unit model may both be used, along with certain patient and facility information, to predict the patient's length of stay in an emergency department.

The length-of-stay model utilizes a machine learning algorithm to make the prediction of a particular patient's length of stay within a department, such as the emergency department. In exemplary embodiments, the length-of-stay model uses a gradient boosted tree (which may be referred to as xgboost) algorithm. It is contemplated that, in alternative embodiments, other machine learning methods, such as random forest, logistic regression, neural network, and the like, may be used.

As previously mentioned, there are several factors, also referred to herein as features, that may affect a patient's length of stay within a particular department. For instance, for the emergency department, a patient's length of stay may be affected by patient demographics (e.g., gender, age); insurance information; arrival time and arrival mode (ambulatory vs. other); assigned acuity score; arrival diagnosis (also referred to as the reason for visit); pregnancy, including a pregnancy of over 20 weeks; patient history, including past emergency department utilization, past inpatient utilization, past lengths of stays; current emergency department volume; current inpatient volume; staffing; and current queue position. Multiple features may be used as input into the length-of-stay model. By using a variety of features, the length-of-stay model increases the accuracy compared to conventional solutions that only consider one feature at a time in estimating a length of stay.

As previously stated, the length-of-stay model disclosed herein may utilize gradient boosted decision tree learning to predict a target patient's length of stay based on a number of features. In using a gradient boosted regression tree, the predicted length-of-stay outputs may be provided as continuous numbers. In accordance with the gradient boosted tree model, different features may be used along different paths, and those features may be used to identify one or more populations of other people with some commonality with the target patient based on those features. In other words, at the end of the gradient boosted tree, a particular patient may be classified into one or more bins representing populations of people with some level of similarity to the patient, and each bin may be associated with a length of stay determined by the actual lengths of stays for the people belonging within the bin. In an exemplary embodiment, the length of stay associated with each bin is the average length of stay.

A target patient may be found to belong to multiple bins based on similarities of different features. As such, the average length of stay for each bin to which the target patient belongs may be combined to provide the predicted length of stay for the target patient. In one embodiment, the lengths of stays associated with each bin may be further averaged together to determine the predicted length of stay for the target patient. In some embodiments, the bins may have different weights based on the features utilized for classification within the bin, and, as such, the average length of stay for each bin may be weighted when combined to predict the target patient's length of stay.

In exemplary aspects, the average lengths of stays for each population bin may be updated with more recent data from a reference population. This information may be updated continuously, periodically, or on an as-needed basis. In some embodiments, the average lengths of stays are updated as new reference data is being received in real time or in near real time. Using the most current information from reference populations allows the prediction for a target patient's length of stay to be more accurate.

As previously stated, there are multiple features that may impact a patient's length of stay, and, thus, values for multiple features may be input into the length-of-stay model. In exemplary aspects, some of the features are derived features in that they are transformed outputs of one or more other prediction models as previously discussed. Additionally, some of the feature values used for the initial models and/or length-of-stay model may be derived from patient and/or facility information. Other feature values may be directly from the received patient and/or facility information. In one embodiment reduced to practice, the following derived features were used as input in the length-of-stay predictor for the emergency department:

Logit(initial admit probability);
Logit(initial telemetry probability);
Logit(initial predicted service line of unspecialized);
Log1p(past inpatient encounters)—based on a count of past inpatient encounters;
Has past inpatient encounter;
Log1p(past ED encounters)—based on a count of past emergency department encounters;
Has past ED encounter;
Arrival is ambulatory; and
Arrival is nightshift.

Accordingly, output predictions from the initial models (e.g., admission model and facility unit model) may be transformed such that the log of the odds ratio of the predictions are used as input for the length-of-stay model. Additionally, the natural logarithm plus 1 (Log1p) may be used to transform other data into input features for the length-of-stay model. Other features may be data transformed into a binary value. For instance, whether a target patient has a past inpatient or ED encounter, whether the arrival is ambulatory, and whether the arrival is during the nightshift may be binary features. These transformation may be performed so that the inputs for the length-of-stay model are more linear. Alternatively or additionally, non-derived features may be used for the length-of-stay model. For instance, the actual time of arrival expressed in a time value may be used as an arrival time feature instead of a binary value for whether the patient arrived during the nightshift. Additionally, a patient's age, arrival acuity, and current department volume may have feature values input into the length-of-stay predictor directly from the received patient information or facility information.

Figure 3A:
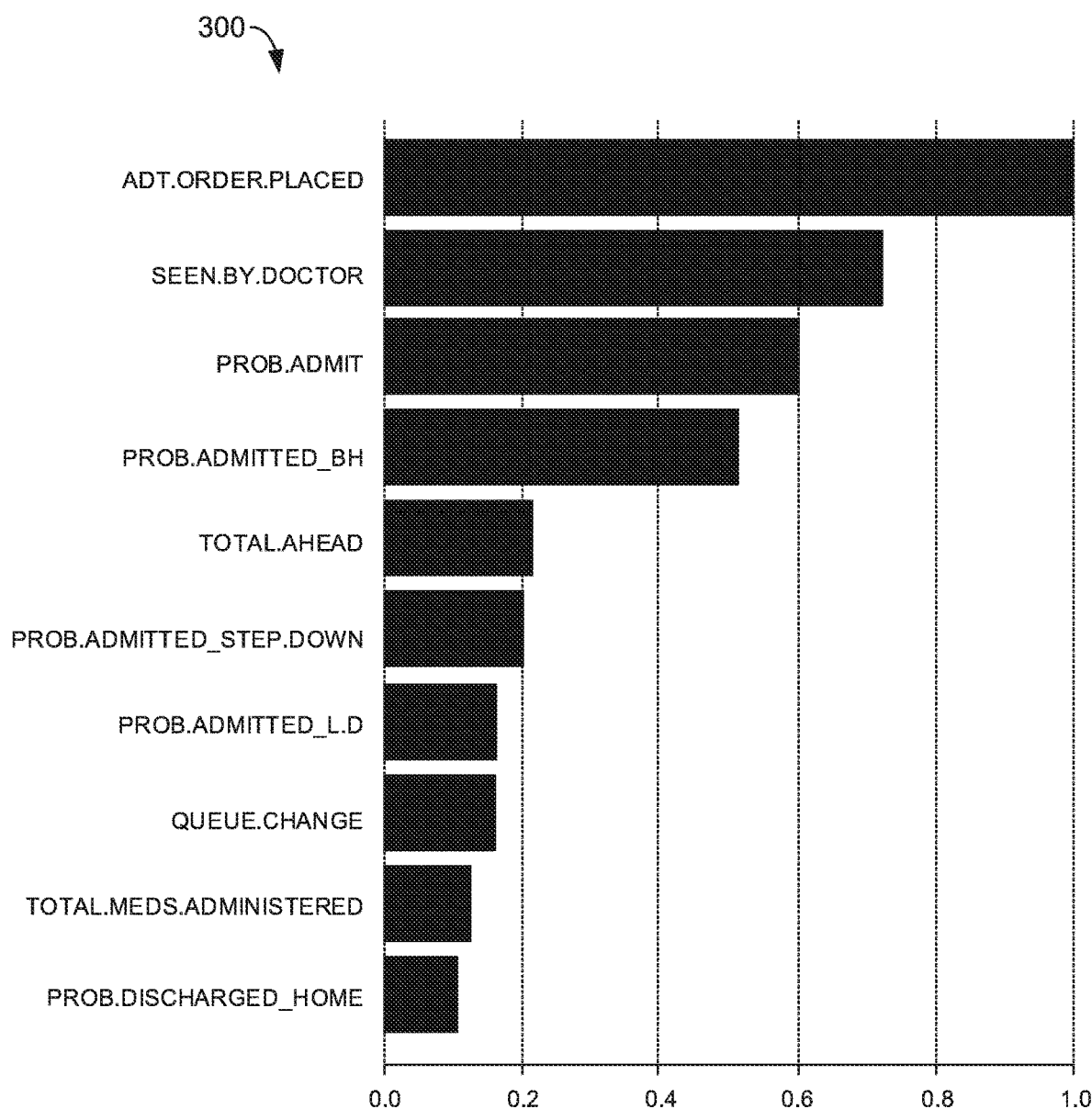
FIGS. 3A and 3B illustrate the relative contributions of features in predicting a length of stay in embodiments of the disclosure actually reduced to practice.
Figure 3B:
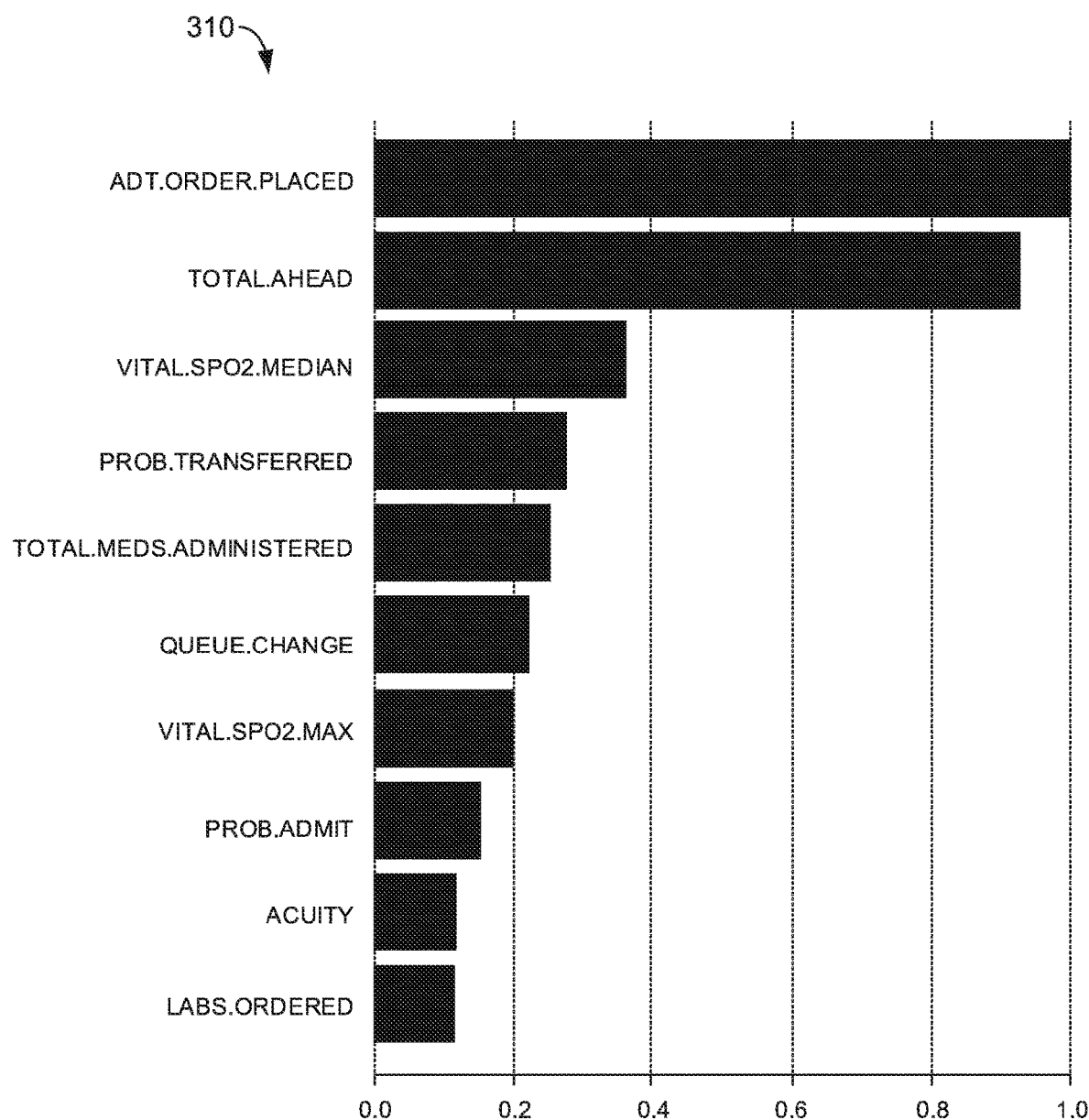

The degree of impact of each feature on the predicted length of stay may vary. FIGS. 3A-3B depict the variable importance, or the relative contribution, of a number of features to embodiments of a length-of-stay model. FIG. 3A depicts a graphical illustration 300 of the variable importance for a first embodiment actually reduced to practice for a first healthcare facility, and FIG. 3B depicts a graphical illustration 310 of the variable importance for a second embodiment actually reduced to practice for a second healthcare facility. As illustrated, the predictions from initial predictive models, such as probabilities of admission (generally), admission to behavioral health, admission to a step down unit, and admission to a labor and delivery unit, are included in the top features having the most variable importance for the first embodiment at the first facility. Other top features for the first facility include additional orders placed, whether the patient had been seen by a physician, the number of patients currently ahead in the emergency department queue (i.e., queue position), queue change, and total number of medications administered. The features with the most variable importance in the second facility were a different set of features that included additional orders placed, vital signs (median and maximum values), probability of being transferred, total medications administered, queue change, probability of being admitted (generally), acuity level, and labs ordered. As reflected in FIGS. 3A and 3B, different features may have different variable importance levels for different facilities, which reflect that each facility and department may be run in different manners. To accommodate the uniqueness of each facility, in some aspects, the length-of-stay model may be trained with data for a particular facility to capture the most important features for that facility.

Figure 4:
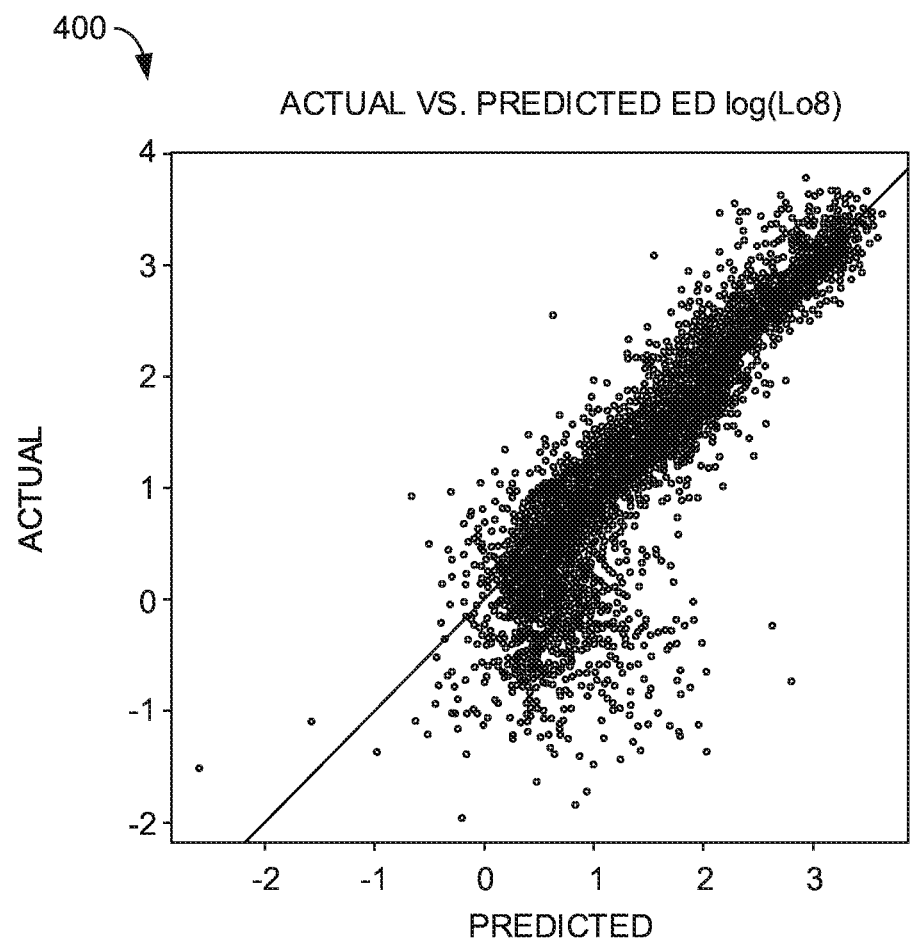
FIG. 4 illustrates the accuracy of an embodiment of a length-of-stay model actually reduced to practice in accordance with this disclosure.

Rather than using the conventional factor-by-factor approach, the modeling technique used for predicting a length of stay described herein incorporates multiple features at once. This machine learning technique has been found to result in a more accurate prediction for a target patient's length of stay. FIG. 4, for instance, shows a graphical representation 400 of the statistical performance of an embodiment of the length-of-stay model actually reduced to practice. As illustrated, the statistical model fitting in graphical representation 400 illustrates that the predicted lengths of stays tended to be close to the actual lengths of stay. Additionally, in one embodiment with a first data set, the mean absolute error (MAE) and the root mean squared error (RMSE) for the predictor was found to be 0.69 hours (41 minutes) and 1.32 hours (79 minutes), respectively. In another embodiment using a second data set, the MAE and the RMSE for the predictor was found to be 0.37 hours (22 minutes) and 1.1 hours (66 minutes), respectively.

Returning to method 200, at step 240, a response action is initiated based on the predicted length of stay. The response action may comprise one or more of generating and communicating an electronic notification with the expected length of stay to one or more persons. For instance, a staff member, the patient, and/or one or more caregivers of the patient (including friends and family for whom the patient has consented receiving information) may be notified of the predicted length of stay within the emergency department. In some embodiments, a patient's predicted length of stay may change based on changes to the patient's treatment (e.g., additional tests being ordered), changes to the status of the emergency department (e.g., unexpected change in volume due to other patients leaving), or changes to the status of the facility (e.g., unexpected staffing changes for inpatient units). As such, the patient's length of stay may be predicted multiple times as patient information and/or facility information is updated, and as such, one response action may be to electronically transmit a notification of an updated predicted length of stay. The notification may be transmitted to a device associated with the intended recipient, such as a notification via e-mail, telephone call, SMS text, or an application notification, including a notification via a patient portal application on a client device.

In some embodiments, the predicted length of stay for a particular patient is compared to a threshold length and, if the predicted length satisfies the threshold length, an alert may be transmitted to one or more staff members of the department. This threshold length may represent a sufficiently long length of stay that warrants monitoring by one or more staff members. As such, in some aspects, the threshold length is satisfied if the predicted length of stay for a particular patient meets or exceeds the threshold length. For instance, in some embodiments, when a patient's predicted length of stay meets or exceeds the threshold length, an alert may be sent to a designated staff member, such as an emergency department manager or head nurse. Alerting a department staff member of a length of stay that satisfies a threshold may allow the staff to more closely monitor the patient and take additional measures to help minimize the patient's length of stay.

In addition to or as an alternative to an electronic notification or alert, initiating a response action based on a predicted length of stay may include a resource management action, such as automatically reallocating resources, such as staff, space, supplies, equipment, and medications. In some embodiments, resources may be allocated to the patient or to the department in which the patient is in when a patient's predicted length of stay satisfies a threshold length of stay. For instance, a floating nurse may be assigned to the patient, which may help move along the patient's care process and, thus, minimize the patient's length of stay.

Figure 5:
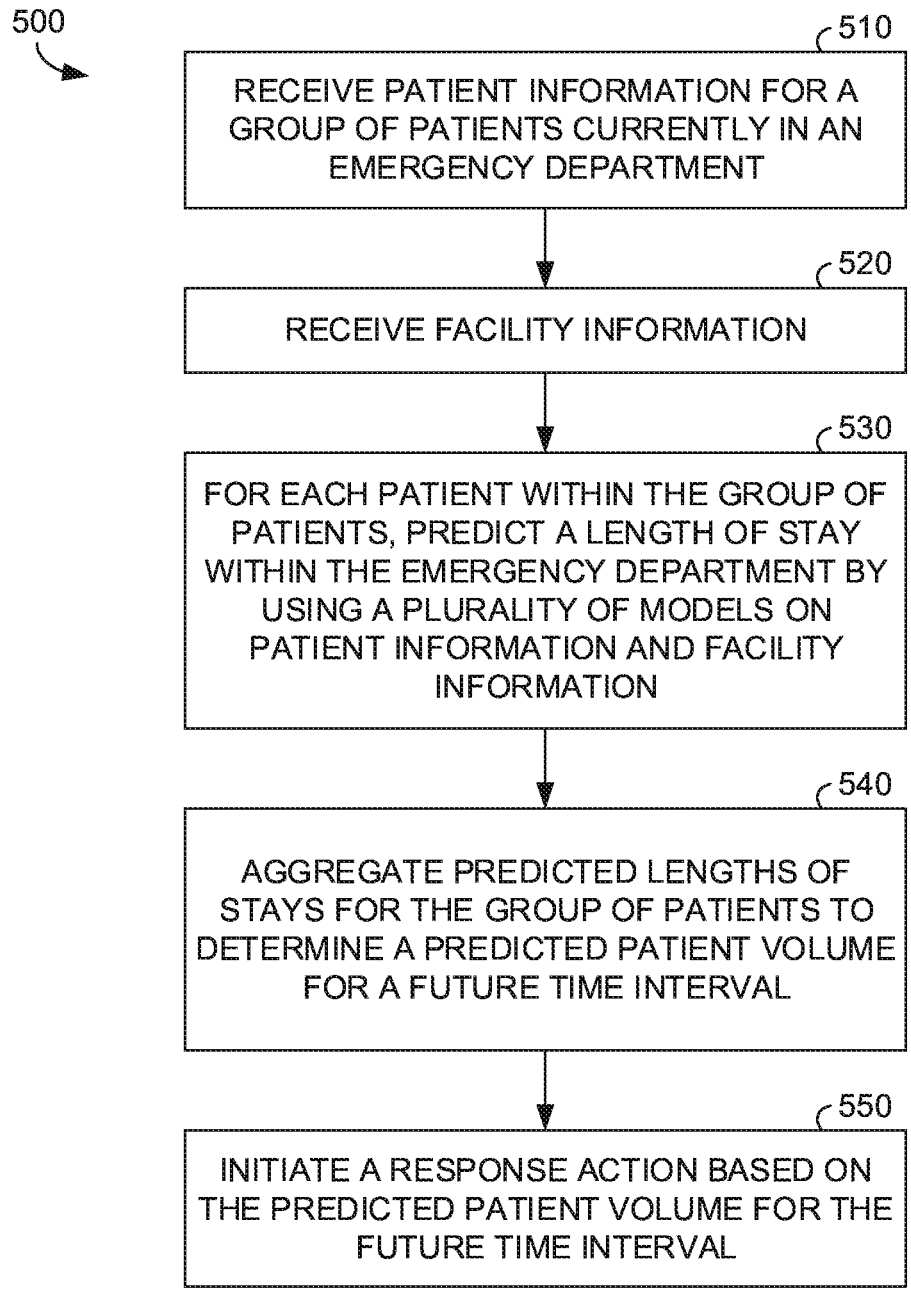
FIG. 5 depicts a flow diagram of a method for managing department resources using predicted lengths of stays, in accordance with an embodiment of the disclosure.

Department resources may be further managed through one or more response actions based on lengths of stays predicted for multiple patients. As such, FIG. 5 depicts a flow diagram of a method 500 for automatically managing resources within an emergency department based on predicted lengths of stays of patients within the department in accordance with an embodiment of the disclosure. At step 510, patient information for a group of patients is received. The group of patients may be individuals currently within the emergency department and may include individuals who have gone through registration. These patients may be currently being treated, waiting to be treated or examined, or waiting for a transfer, discharge, or admittance to another unit within the facility. At step 520, facility information may be received. The patient information for each patient and facility information may include the information described above with respect to method 200 and may be received in a similar manner At step 530, a length of stay within the emergency department may be predicted for each patient within the group of patients. The length of stay may be predicted by performing sequential modeling using at least some of the received patient information and facility information. This step may be similar to the process for predicting a length of stay described with respect to method 200 and FIGS. 2-4.

At step 540, an overall patient volume for the emergency department may be predicted for a future time interval using the predicted lengths of stays for all patients within the group. In some embodiments, this process includes, for each patient, identifying the start time of the patient's length of stay, which may be the time the patient was registered at triage. This information may be part of the patient information received in step 510. Using the start time and the predicted length of stay for that patient, a predicted departure time for the patient may be estimated. Using the estimated departure time for each patient within the group, an expected volume of patients may be identified based on when the current patients are predicted to leave the emergency department either through being transferred, discharged, admitted into another unit, or simply leaving. The predicted volume of patients may be for a future time interval, such as within the next 1 hour, 2 hours, 5 hours, 12 hours, 24 hours, or other time interval.

Additionally, as it could be expected that additional patients may come into the emergency department within that future time interval, predicting the patient volume may also include estimating a number of new patients to arrive during that future time interval and assigning a length of stay to those patients. Estimating the new number of patients may be done based on historical data. For instance, if the future time interval is between 8 am and 8 pm on a Tuesday night, the average number of patients that arrive in the emergency room during that time interval may be determined from historical data, and each anticipated new patient may be assigned a length of stay equal to an average length of stay. This information may be used in combination with the predicted lengths of stay of current patients to predict the patient volume within the department during that future time interval.

Continuing with method 500, at step 550, one or more response actions may be initiated based on the predicted patient volume within the future time interval. These one or more response actions may be automatically initiated and may be similar to actions initiated in method 200, such as generating and electronically transmitting a notification or an alert. In some embodiments, the notification may comprise a notification of the predicted patient volume to one or more healthcare providers or staff members of the emergency department or healthcare facility. Additionally, in some embodiments, a notification or alert is initiated only upon determining that the predicted patient volume satisfies a threshold volume.

Further, in some embodiments, the one or more response actions include automatically allocating resources for the emergency department. As discussed with respect to FIG. 2, resources may include staff, space (i.e., patient beds), supplies, equipment, and medications. For instance, if the predicted volume within the future interval exceeds a threshold volume, a request for additional equipment, supplies, or medications may be automatically transmitted. This request may be sent to another unit within the facility or to a third-party vendor. In some embodiments, the additional resources that are requested include equipment, supplies, or medications that are commonly or most frequently used. In some embodiments, the resources that are requested are based on current inventory levels. For instance, in one embodiment, a resource may be automatically requested only when both the anticipated patient volume exceeds a threshold volume and when current inventory for that resource is below a threshold amount.

With respect to staffing resources, additional staff, such as nurses, technicians, patient care assistants, nursing assistants, and other caregivers, may be automatically requested when the predicted patient volume satisfies a threshold volume. In some embodiments, this request is automatically initiated only upon the predicted patient volume satisfying a threshold volume and the current or scheduled staffing levels meeting or being below a minimum staffing level. The request for additional staff may be a request for staff from other units within the facility and/or may initiate an electronic system for calling in staff members who are not currently working, such as on-call staff members. In some embodiments, the response action includes adjusting a staffing schedule that covers the future time interval.

Figure 6:
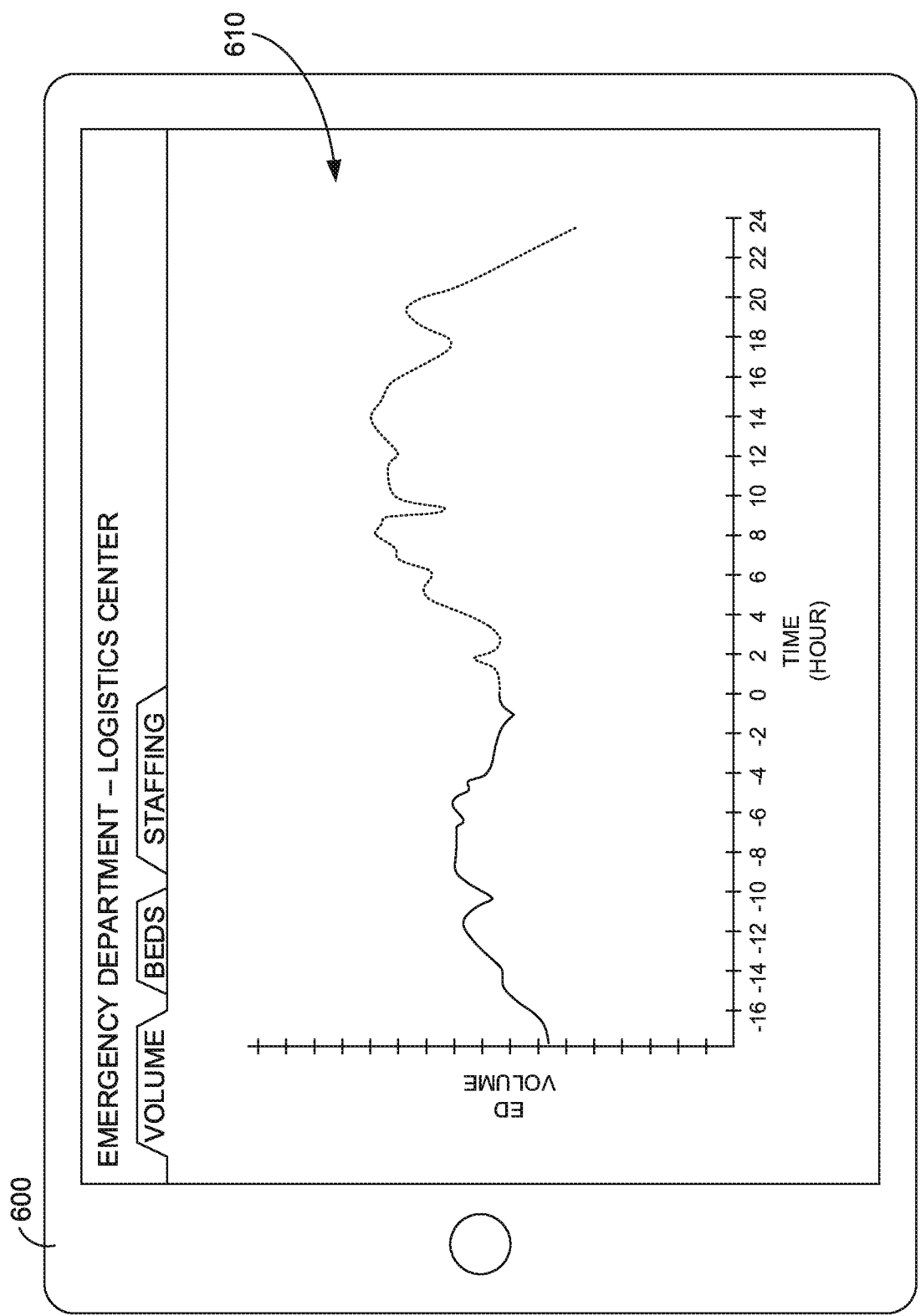
FIGS. 6-8 depict graphical user interfaces generated through predictions of patient lengths of stays, in accordance with embodiments of the disclosure.
Figure 7A:
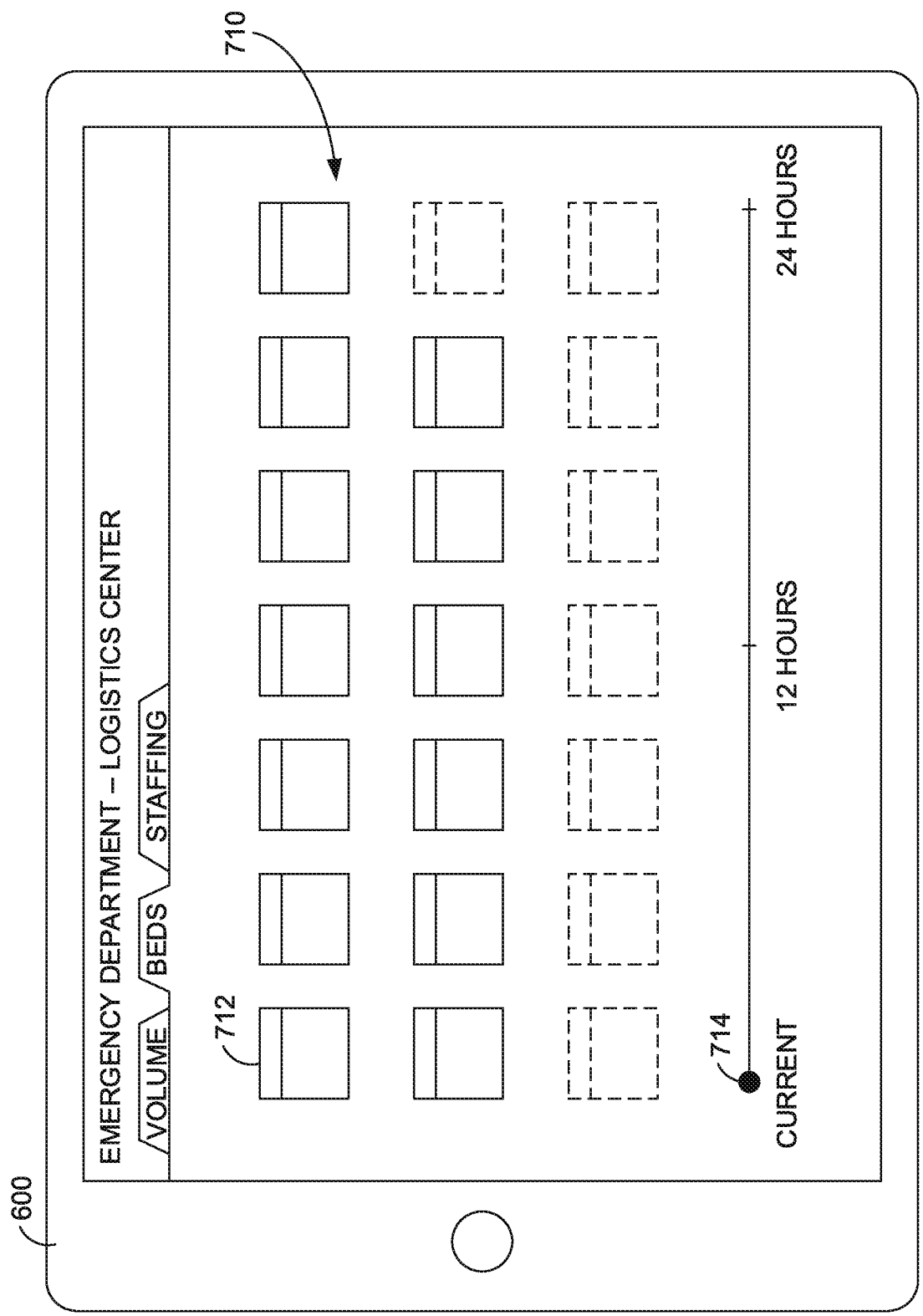
Figure 7B:
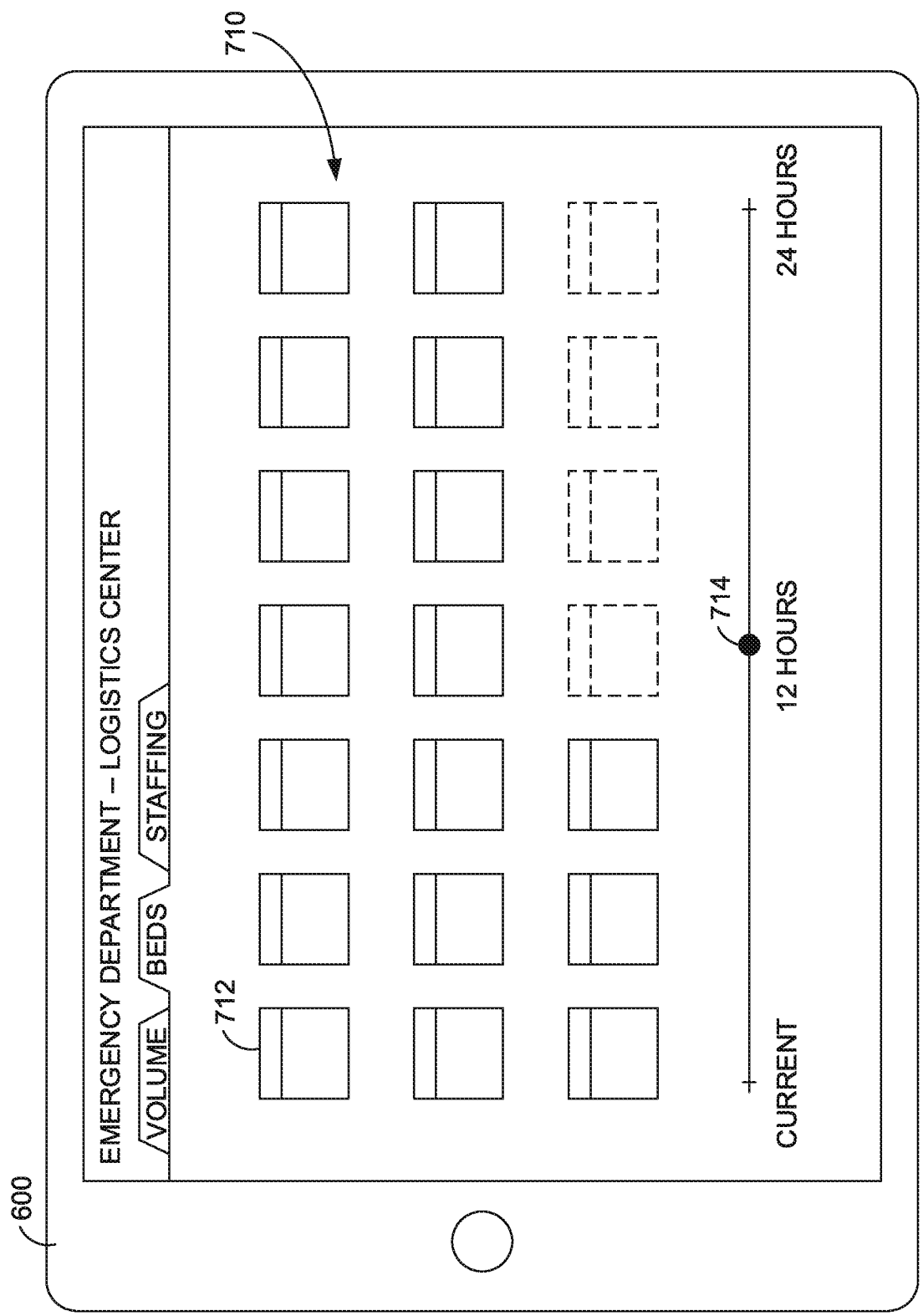
Figure 7C:
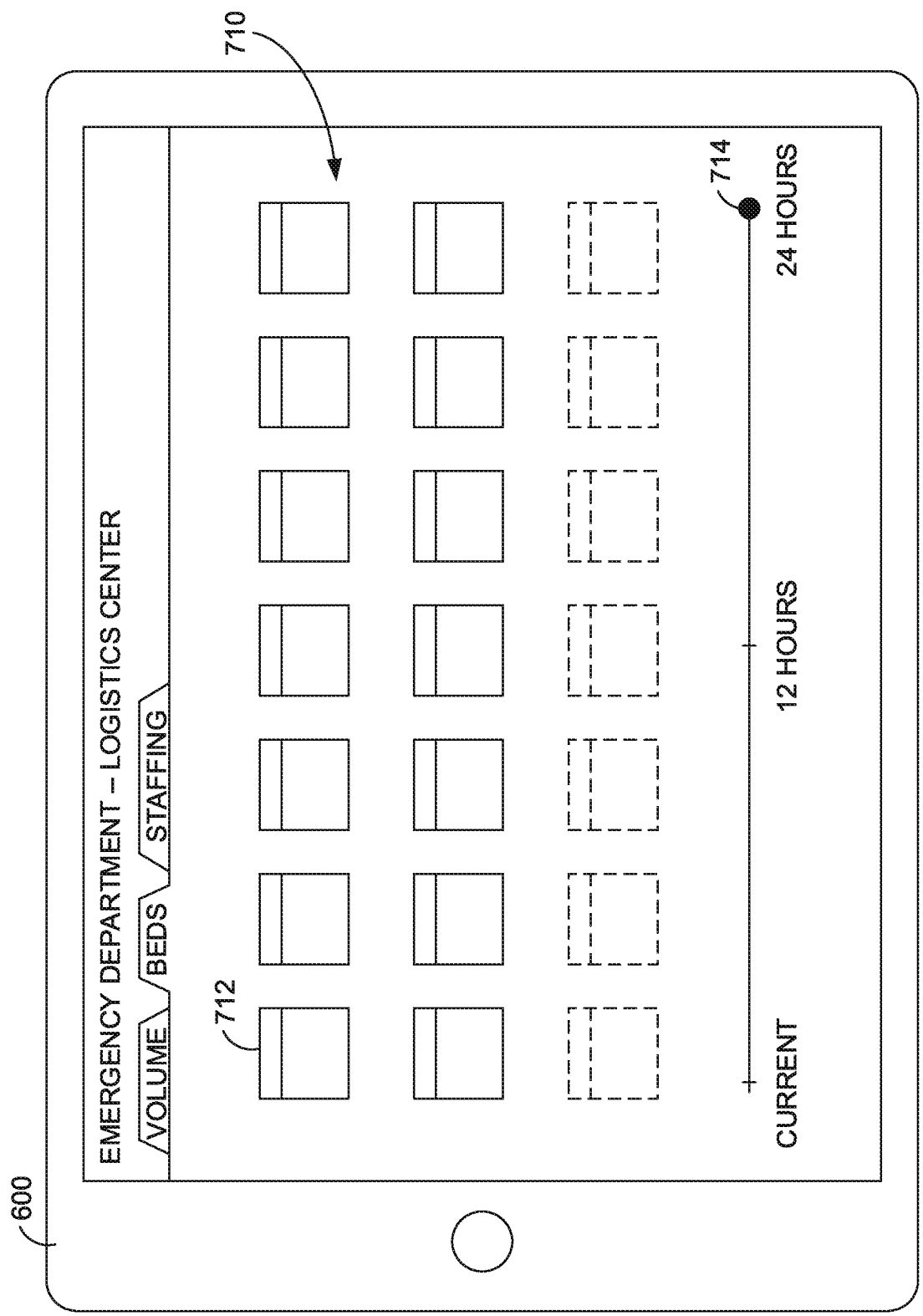
Figure 8:
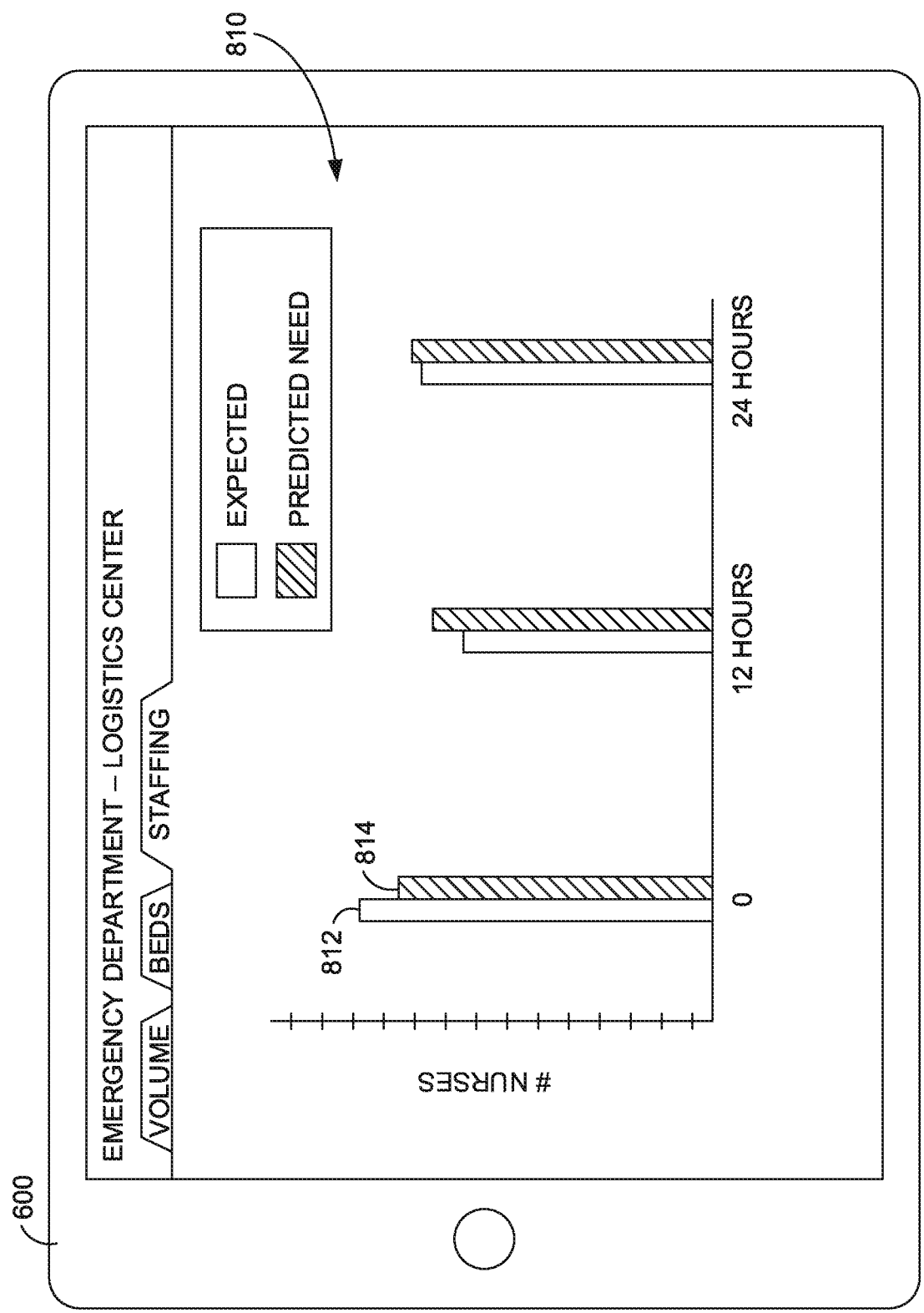

Turning to FIGS. 6-8, one or more graphical user interfaces generated in accordance with embodiments of the present disclosure are provided. These user interfaces may help a user, such as a healthcare provider, more effectively and efficiently manage resources for a healthcare unit, such as the emergency department, using predicted lengths of stays for patients. User interfaces discussed with respect to FIGS. 6-8 may operate in a similar manner as user interface 141 of FIG. 1A. Additionally, the user interfaces may be generated for presentation on a user device, such as user device 600. User device 600 in FIGS. 6-8 may be similar to computer systems discussed with respect to FIGS. 1A-B.

User device 600 may run, either remotely or over a connected system, a decision support application, such as application 140 in FIG. 1A, for managing resources within the emergency department. Graphical user interfaces generated based on the predicted lengths of stays may be provided on the user device 600 through the decision support application. Accordingly, one or more embodiments of the present disclosure includes a computing system for providing a user interface for an emergency department decision support tool. The system may include a display component, one or more processors, and computer storage media with instructions for generating the user interface. The instructions may cause the processors to determine lengths of stay in an emergency department that are predicted for a plurality of patients. Each length of stay may be predicted using sequential modeling as discussed above with respect to FIGS. 2-5. In some embodiments, the operations for making the predictions for the lengths of stay may be performed by the computing system itself or may be received from a remote server. Further, a graphical user interface may be generated for display on the display component using the predicted lengths of stays. The graphical user interface may be generated to include one or more user interface elements. These user interface elements may visually represent measurements of one or more resources for a future time interval based on the predicted lengths of stay as further shown in FIGS. 6-8. Further, the user interface elements may be automatically updated as new predictions are made based on new patient and/or facility information or as the time interval changes, either through the passage of time or upon adjustment of a selectable time component on the user interface.

FIG. 6, for instance, depicts a graphical user interface 610 illustrating overall patient volume. Graphical user interface 610 includes user interface elements showing the volume of patients within the emergency department over time. As illustrated, the time may include a past time and a future time interval. As such, the user interface 610 informs a user of actual volume and predicted volume. User interface 610 illustrates actual volume with a solid line and predicted volume with a dashed line, but it is contemplated that alternative or additional visual features may be used to distinguish between actual and predicted volumes.

FIGS. 7A, 7B, and 7C depict a graphical user interface 710 showing predicted bed space available as determined by the predicted volume of patients with the emergency department. User interface 710 may include user interface elements in the form of bed icons 712 each representing a bed space within an emergency department and one or more time interval selectors, such as slider 714. In some embodiments, the user interface elements may be selectable. For instance, bed icons 712 may be selected to identify a particular bed space (i.e., patient room) and, in some aspects, identify information about a patient assigned to an occupied bed. Slider 714 may be selected to adjust the time frame of reference. For instance, slider 714 may indicate a current time or a specified future time. In some aspects, slider 714 may also be selected to show a past time.

Each bed icon 712 may visually indicate whether the bed is available based on actual and/or predicted patient volume. In the example user interface 710, occupied (either actual or predicted) beds are represented with bed icons 712 of solid lines while available beds are represented bed icons 712 of dashed lines. For instance, in FIG. 7A, when slider 714 is set to the current time, there are 13 occupied beds and 8 available beds. These counts may be based on actual patient volume at the current time. As a user moves the slider 714 to future time intervals, user interface elements, such as bed icons 712 may be updated to represent available and or occupied beds at the later time based on predicted patient lengths of stays, as shown in FIGS. 7B and 7C.

FIG. 8 depicts a graphical user interface 810 that includes user interface elements visually representing the difference between levels of expected/scheduled staff members, such as nurses, and a recommended level based on predicted patient volumes. In the embodiment illustrated, user interface elements include solid bars 812 representing expected number of nurses at certain times and striped bars 814 representing recommended numbers of nurses based on patient volumes predicted for those times. Graphical user interface 810 may also include one or more selectable buttons for requesting additional staff where such additional staff is recommended based on the predicted patient volumes.

Many different arrangements of the various components depicted, as well as components not shown, are possible without departing from the spirit and scope of the present invention. It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. A computerized method for managing healthcare resources within an emergency department, the computerized method comprising:
   receiving patient information for a plurality of patients being admitted into an emergency department;
   receiving facility information for a facility in which the emergency department is located;
   predicting a length of stay in the emergency department for each patient within the plurality of patients, each length of stay being predicted using a plurality of machine learning models and at least some of the patient information and at least some of the facility information, wherein the length of stay is predicted by using the plurality of machine learning models in a sequence, such that an output from one of the plurality of machine learning models is an input for a subsequent machine learning model of the plurality of machine learning models; and
   automatically initiating one or more response actions based on the lengths of stays predicted for the plurality of patients.

2. The computerized method of claim 1, wherein the method further comprises using the lengths of stays predicted for the plurality of patients to predict a patient volume for the emergency department for a future time interval, and wherein initiating the one or more response actions based on the lengths of stays comprises initiating one or more response actions based on the predicted patient volume.

3. The computerized method of claim 2, wherein the one or more response actions comprises adjusting a staffing schedule for the future time interval.

4. The computerized method of claim 1, wherein the one or more response actions comprises requesting additional supplies.

5. The computerized method of claim 1, wherein predicting the length of stay for each patient using the plurality of machine learning models comprises determining one or more initial predictions for variables relating to a stay of the patient, each initial prediction being determined using a different model based on at least some of the patient information and at least some of the facility information and using the one or more initial predictions to predict the length of stay with a length-of-stay model.

6. The computerized method of claim 5, wherein the length-of-stay model comprises a gradient boosted tree model.

7. One or more computer storage media having computer-executable instructions embodied thereon that, when executed, provide a method for managing healthcare resources within an emergency department, the method comprising:
   receiving patient information for a plurality of patients being admitted into an emergency department;
   receiving facility information for a facility in which the emergency department is located;
   predicting a length of stay in the emergency department for each patient within the plurality of patients, each length of stay being predicted using a plurality of machine learning models and at least some of the patient information and at least some of the facility information, wherein the length of stay is predicted by using the plurality of machine learning models in a sequence, such that an output from one of the plurality of machine learning models is an input for a subsequent machine learning model of the plurality of machine learning models; and
   automatically initiating one or more response actions based on the lengths of stays predicted for the plurality of patients.

8. The computer storage media of claim 7, wherein predicting the length of stay for each patient using the plurality of machine learning models comprises:
   for each patient, determining one or more initial predictions for variables relating to a stay of the patient, each initial prediction being computed using a different model within the plurality of machine learning models and based on at least some of the patient information for associated with the patient and at least some of the facility information;
   for each patient, use a length-of-stay model to predict a length of stay for the patient based on the one or more initial predictions for the patient, at least some of the patient information associated with the patient, and at least some of the facility information.

9. The computer storage media of claim 8, wherein the one or more initial predictions for each patient comprises a probability of the patient being admitted into an inpatient unit of the facility, a probability the patient will need a telemetry bed, and a probability that the inpatient unit in which the patient is admitted is a specialized unit.

10. The computer storage media of claim 8, wherein the length-of-stay model comprises a gradient boosted tree model.

11. The computer storage media of claim 7, wherein the one or more response actions comprises transmitting, to a remote user device, one or more electronic notifications indicating a length of stay in the emergency department for each patient within the plurality of patients.

12. The computer storage media of claim 7, wherein the facility information comprises a current staffing level and a staffing level scheduled for a future time interval, each staffing level corresponding to the emergency department.

13. The computer storage media of claim 7, wherein the facility information comprises a current queue position for each of the plurality of patients being admitted into the emergency department.

14. A computerized system for managing healthcare resources within an emergency department, the computerized system comprising:
   one or more processors; and
   one or more computer storage media having instructions that, when executed by the one or more processors, cause a method to be performed, the method comprising:
      receive patient information for a patient being admitted into an emergency department;
      receive facility information for a facility in which the emergency department is located;
      predict a length of stay in the emergency department for the patient, the length of stay being predicted using a plurality of machine learning models and at least some of the patient information and at least some of the facility information, wherein the length of stay is predicted by using the plurality of machine learning models in a sequence, such that an output from one of the plurality of machine learning models is an input for a subsequent machine learning model of the plurality of machine learning models; and automatically initiate one or more response actions based on the length of stay predicted for the patient.

15. The computerized system of claim 14, wherein the input for the subsequent model includes a probability that the patient will be admitted into an inpatient unit.

16. The computerized system of claim 15, wherein the subsequent machine learning model of the plurality of machine learning models predicts the length of stay for the patient.

17. The computerized system of claim 14, wherein the input for the subsequent model includes a probability that the patient will be transferred to another facility.

18. The computerized system of claim 14, wherein the plurality of machine learning models includes a neural network.

19. The computerized system of claim 14, wherein the patient information for the patient being admitted into the emergency department includes demographics, arrival time, arrival mode, arrival diagnosis, and an assigned acuity score.

* * * * *